US00PP24125P3

(12) United States Plant Patent
Probasco et al.

(10) Patent No.: US PP24,125 P3
(45) Date of Patent: Dec. 31, 2013

(54) HOP PLANT NAMED 'HBC 369'

(50) Latin Name: *Humulus lupulus*
Varietal Denomination: HBC 369

(75) Inventors: Eugene G. Probasco, Yakima, WA (US); Jason Perrault, Selah, WA (US)

(73) Assignee: Hop Breeding Company, LLC., Yakima, WA (US)

( * ) Notice: Subject to any disclaimer, the term of this patent is extended or adjusted under 35 U.S.C. 154(b) by 85 days.

(21) Appl. No.: 13/385,388

(22) Filed: Feb. 15, 2012

(65) Prior Publication Data

US 2012/0297512 P1 Nov. 22, 2012

Related U.S. Application Data

(60) Provisional application No. 61/519,359, filed on May 20, 2011.

(51) Int. Cl.
*A01H 5/00* (2006.01)

(52) U.S. Cl.
USPC ..... Plt./236

(58) Field of Classification Search
USPC ..... Plt./236
See application file for complete search history.

(56) References Cited

U.S. PATENT DOCUMENTS

| | | | | |
|---|---|---|---|---|
| PP10,956 | P * | 6/1999 | Lewis et al. | Plt./236 |
| PP13,129 | P2 * | 10/2002 | Probasco | Plt./236 |
| PP13,311 | P2 * | 12/2002 | Probasco | Plt./236 |
| PP21,289 | P3 * | 9/2010 | Probasco et al. | Plt./236 |
| PP23,674 | P2 * | 6/2013 | Jeske et al. | Plt./236 |

OTHER PUBLICATIONS

Probasco et al. "147 HBC 369—A New Flavor Hop Variety" World Brewing Congress Jul. 28-Aug. 1, 2012 available at:http://www.worldbrewingcongress.org/2012/abstracts/AbstractsDetail.cfm?AbstractID=343.*

* cited by examiner

*Primary Examiner* — Wendy C Haas

(57) ABSTRACT

A new hop plant named 'HBC 369' is disclosed. The cones of 'HBC 369' mature in mid September, and yield a crop of 1600 to 2000 pounds per acre. 'HBC 369' is used for its unique aromatic quality, resistance to powdery mildew, high alpha acid content and exceptional yield.

3 Drawing Sheets

Genus and species: *Humulus lupulus.*
Variety denomination: HBC 369.

CROSS-REFERENCE TO RELATED APPLICATIONS

This application claims priority of provisional application Ser. No. 61/519,359.

STATEMENT REGARDING FEDERALLY SPONSORED RESEARCH OR DEVELOPMENT

None

BACKGROUND OF THE INVENTION

'HBC 369' is a product of a controlled breeding program carried out by the inventors in the Yakima Valley of Washington state. 'HBC 369' was one of several seedlings resulting from a cross made in 2001 of female parent 'YCR 14' (patented as 'YCR Accession No. 14 U.S. Plant Pat. No. 12,213) and male parent '986-2' (not patented). A single plant of 'HBC 369' was selected in 2006, and in 2007 was expanded to seven plants, which were then planted in the area of Toppenish, Wash. The plants were observed and evaluated for several years, and in 2010, 70 plants were expanded for further observation and evaluation in the Toppenish, Wash. area. Two one acre test plots of 'HBC 369' were established in 2010 and 2011. Throughout several generations of asexual propagation, 'HBC 369' has been observed to retain its distinctive characteristics and remain true to type.

BRIEF DESCRIPTION OF THE PHOTOGRAPH

Figure 1:
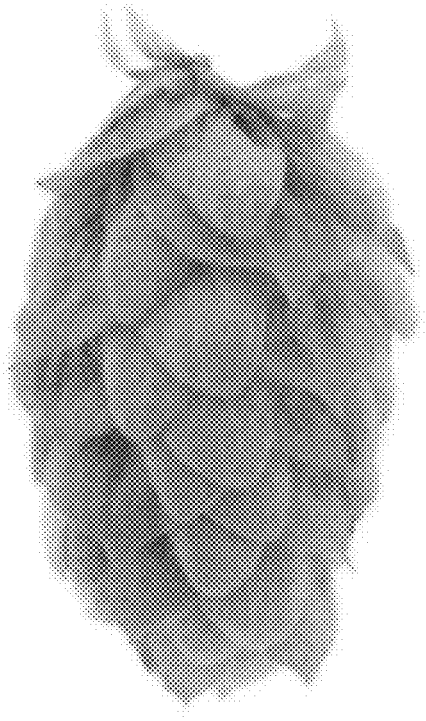
FIG. 1 illustrates a cone of the 'HBC 369 hop plant.
Figure 2:
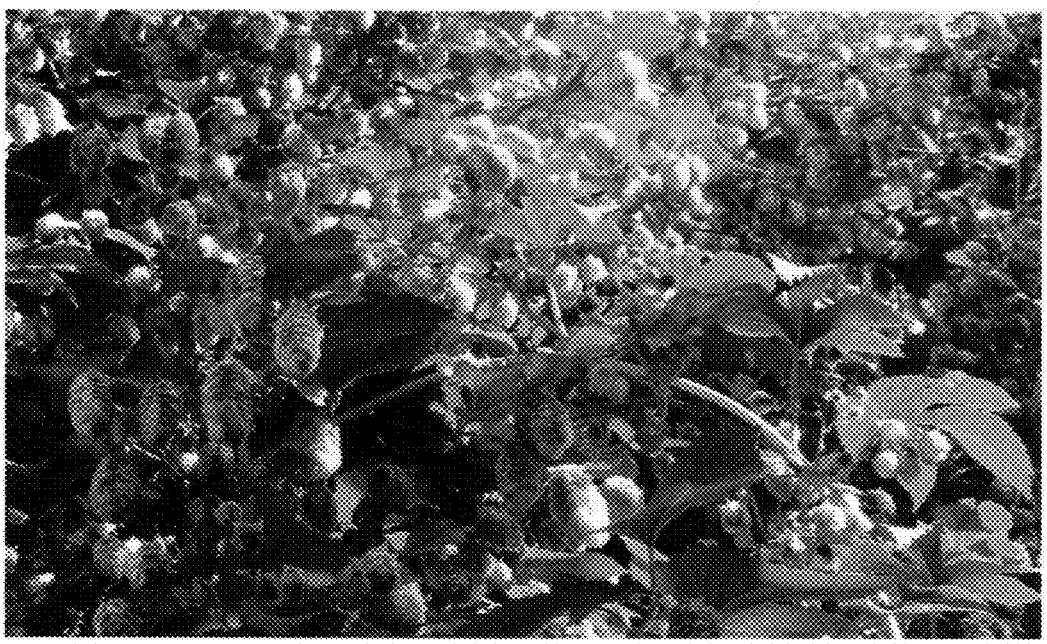
FIG. 2 illustrates leaves and cones of the 'HBC 369' hop plant.
Figure 3:
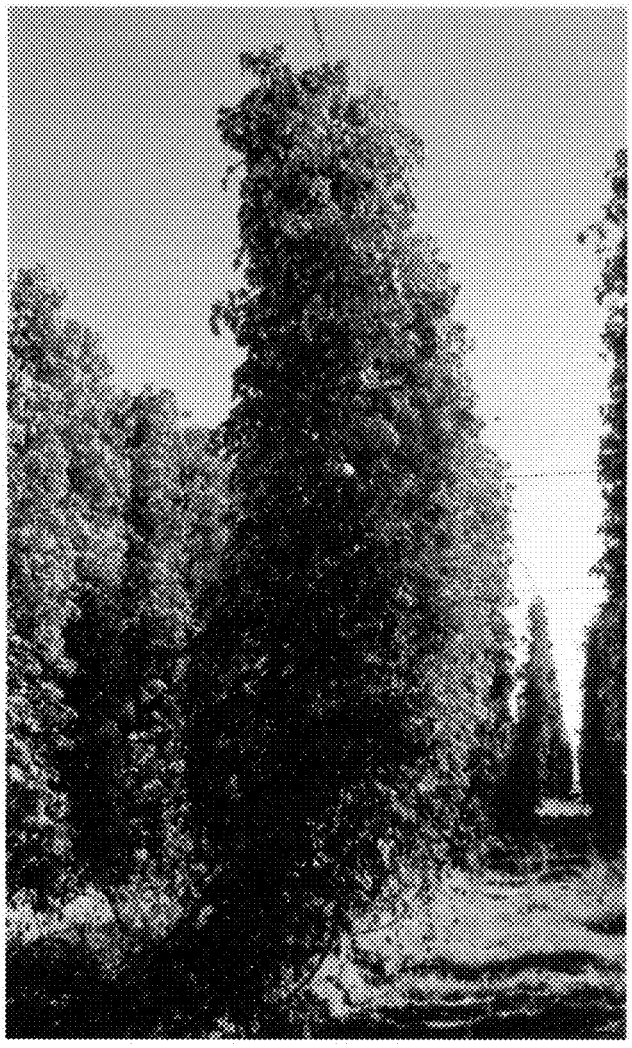
FIG. 3 illustrates a mature 'HBC 369' hop plant grown on a trellis.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2006-2010 growing seasons at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average.

Species: *Humulus lupulus*.
Ploidy: Diploid.
Use: Brewing.
Disease susceptibility: 'HBC 369' is not resistant to hop downy mildew. 'HBC 369' is resistant to powdery mildew.
Pest susceptibility: 'HBC 369' is not resistant to normal infestations of hop aphid and normal infestations of two-spotted spider mite.
Harvest date: September 10-20 (2006-2010 growing season, Toppenish, Wash.).
Crop yield: 2000 pounds per acre.
Bine:
*Color.*—Yellow green 144C.
*Stripe.*—Absent.
*Stipule direction.*—Down-forked.
*Stipule color.*—Yellow green 144A.
*Bine diameter.*—8.4 mm at base; 8.3 mm at 9 feet; 8.0 mm at 18 feet.
Leaf:
*Arrangement.*—Opposite.
*Shape.*—Palmate to Cordate.
*Average length of mature leaf.*—14.8 cm.
*Average width of mature leaf.*—14.3 cm.
*Color of mature leaf upper surface.*—Yellow green 147A.
*Color of mature leaf lower surface.*—Yellow green 147B.
*Color of immature leaf upper surface.*—Yellow green 147A.
*Color of immature leaf lower surface.*—Yellow green 147B.
*Number of lobes.*—1-7.
*Margin.*—Serrate.
*Serrations per inch.*—4.3.
*Average petiole length* (*mature*).—11.1 cm.
*Petiole color at base.*—Yellow green 144C.
*Venation.*—Palmate.
*Vein color.*—Yellow green 144C.
Cone:
*Average weight.*—790 mg.
*Average length.*—3.5 cm.
*Average diameter.*—2.0 cm.
*Bract tip color.*—Yellow green 144B.
*Bract base color.*—Yellow green 149D.
*Bracteole color.*—Yellow green 149D.
*Cone shape.*—Ovoid.
*Bract shape.*—Ovate.
*Bract tip shape.*—Cuspidate.
*Bract tip position.*—Loosely Appressed.
*Bracteole shape.*—Ovate.
*Pickability.*—Good.
*Aroma.*—Blueberry, citrus, fruity, tropical, floral.
*Cone storage.*—15-20% loss of soft resins after 6 month storage at room temperature.
Analytical characteristics:
*Alpha acid* (*as % of cone weight*).—11.5% to 13.5%.
*Beta acid* (*as % of cone weight*).—3.2% to 3.9%.
*Cohumulone* (*as % of alpha acids*).—24% to 26%.
*Total oil.*—1.5 mL per 100 g hops.
*Storageability.*—60% to 65% loss of alpha acids after 6 months storage at room temperature.
Essential oil profile—See Table 1.

TABLE 1

Essential Oil Profile of 'HBC 369' - Gas Chromatogram

| Component | % |
|---|---|
| β-pinene | 0.95 |
| Myrcene | 54.11 |
| 3-methyl-butyl isobutyrate | 0.11 |
| Linalool | 0.68 |
| Caryophyllene | 6.44 |
| Farnesene | 0.06 |
| Humulene | 13.20 |
| Geraniol | 1.16 |

What is claimed is:

1. A new and distinct hop plant as shown and described herein.

* * * * *